United States Patent [19]

McGuire et al.

[11] Patent Number: 4,525,252
[45] Date of Patent: * Jun. 25, 1985

[54] METHOD FOR SYNTHESIZING $N_2O_5$

[75] Inventors: Raymond R. McGuire, Brentwood; Clifford L. Coon, Fremont; Jackson E. Harrar, Castro Valley; Richard K. Pearson, Pleasanton, all of Calif.

[73] Assignee: The United States of America as represented by the United States Department of Energy, Washington, D.C.

[*] Notice: The portion of the term of this patent subsequent to Apr. 17, 2001 has been disclaimed.

[21] Appl. No.: 546,715

[22] Filed: Oct. 28, 1983

Related U.S. Application Data

[62] Division of Ser. No. 399,948, Jul. 20, 1982, Pat. No. 4,432,902.

[51] Int. Cl.³ ............................................. C25B 1/00
[52] U.S. Cl. .................................... 204/101; 204/103
[58] Field of Search ................. 204/59 R, 101, 103

[56] References Cited

U.S. PATENT DOCUMENTS 4,443,308  4/1984  Coon et al. ..................... 204/101

FOREIGN PATENT DOCUMENTS 231546  2/1911  Fed. Rep. of Germany .

OTHER PUBLICATIONS

J. Zawadski et al, "Electrochemical Preparation of Nitrogen Pentoxide", *Rocznki Chemii*, 22 (1948), 233.

Primary Examiner—John F. Niebling
Attorney, Agent, or Firm—Paul Davis; Harold M. Dixon; Judson R. Hightower

[57] ABSTRACT

A method and apparatus for electrochemically synthesizing $N_2O_5$ includes oxidizing a solution of $N_2O_4$/$HNO_3$ at an anode, while maintaining a controlled potential between the $N_2O_4$/$HNO_3$ solution and the anode. A potential of about 1.35 to 2.0 V vs. SCE is preferred, while a potential of about 1.80 V vs. SCE is most preferred. Thereafter, the $N_2O_5$ is reacted with either 1.5-diacetyl-3,7-dinitro-1,3,5,7-tetraazacyclooctane (DADN) or 1,3,5,7-tetraacetyl-1,3,5,7-tetraazacyclooctane (TAT) to form cyclotetramethylenetetraamine (HMX).

9 Claims, 5 Drawing Figures

METHOD FOR SYNTHESIZING $N_2O_5$

BACKGROUND OF THE INVENTION

The U.S. Government has rights in this invention pursuant to Contract W-7405-ENG-48 between the U.S. Department of Energy and the University of California, for the operation of the Lawrence Livermore National Laboratory.

This is a division of application Ser. No. 399,948 filed Jul. 20, 1982 now U.S. Pat. No. 4,432,902.

The present invention relates generally to a method and apparatus for synthesizing $N_2O_5$ and cyclotetramethylenetetraamine (hereinafter referred to as HMX), and more particularly to a method and apparatus for synthesizing these compounds electrochemically utilizing a controlled potential applied between the anode and the $N_2O_4/HNO_3$ solution disposed at the anode. The subject matter disclosed and claimed herein relates to the subject matter disclosed and claimed in our U.S. Pat. No. 4,443,308.

HMX is a powerful high explosive possessing significant advantages in both explosive performance and thermal stability over other explosives such as cyclotrimethylenetrinitraamine (hereinafter referred to as RDX). In comparison to RDX, HMX is: more stable thermally and thereby offers substantially better fire safety characteristics; yields a greater energy per unit weight when burned; and evolves more gas per unit volume. These qualities have made it an attractive candidate for a variety of military uses. Unfortunately, HMX is substantially more expensive and difficult to synthesize than RDX.

In one method of HMX synthesis, a mixture of hexamethylenetetramine (hexamine), acidic anhydride, and ammonium acetate is reacted to form diacetylpentamethylenetetramine (hereinafter referred to as DAPT), produced as a solution in acetic acid. This crude solution is then added to a mixture of nitric and sulfuric acids, where it is converted to 1,5-diacetyl-3,7-dinitro-1,3,5,7-tetraazacyclooctane (hereinafter referred to as DADN). This product is recovered in high yield (94%, based on hexamine). In a subsequent nitrolysis step, the DADN is heated with $N_2O_5$ (dinitrogen pentoxide), forming HMX. The process is illustrated in the following equation:

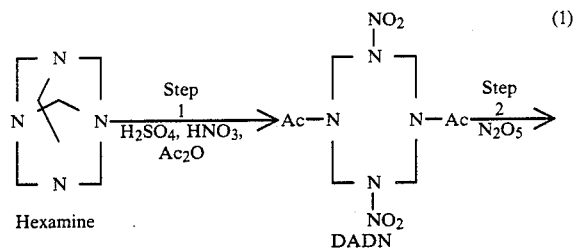

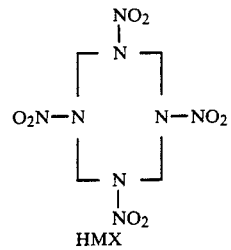

Another method of HMX synthesis is disclosed in U.S. Pat. No. 3,926,953, dated Dec. 16, 1975, to Coburn, et al. This patent discloses that the violent exotherm which results from the nitrolysis of DAPT to DADN with near stoichiometric concentration of nitric acid is completely eliminated by the addition of urea to the crude solution of DAPT in acetic acid prior to the nitrolysis.

The most difficult and costly step in the HMX processes outlined above is the preparation of $N_2O_5$. One method of synthesizing $N_2O_5$ is by the dehydration of $HNO_3$ using polyphosphoric acid, as illustrated by the following equation:

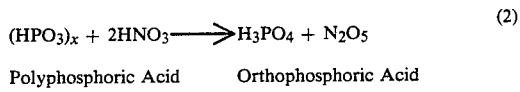

A limitation of the $N_2O_5$ synthesis outlined above is the cost of recycling the orthophosphoric acid to polyphosphoric acid.

Investigators in Germany and Poland have reported that $N_2O_5$ can be produced by electrolyzing a solution of $N_2O_4$ (dinitrogen tetroxide) in anhydrous nitric acid, German Pat. No. 231,546 1910; and J. Zawadski and Z. Bankowski, "Electrochemical Preparation of Nitrogen Pentoxide" *Roczniki Chemii* 22 (1948), 233. The electrochemical methods of synthesizing $N_2O_5$ as disclosed by these investigators are advantageous because no auxiliary chemical reagents (such as polyphosphoric acid) are required; however, the German and Polish methods fail to recognize the significance of controlled conditions during the electrolysis, particularly maintaining a controlled potential between the anode and the solution disposed adjacent to the anode. A further limitation of these methods is the requirement of nearly anhydrous nitric acid in combination with the $N_2O_4$, e.g., 98–99% $HNO_3$. Additionally, a current efficiency of only about 35% is realized.

It would be a significant advancement of $N_2O_5$, and more particularly HMX synthesis, if an electrochemical method and apparatus could be developed which would eliminate the need for anhydrous nitric acid. It would be another advancement if the side reactions occurring during the oxidation of $N_2O_4$ to $N_2O_5$ could be minimized, and the current efficiency improved.

SUMMARY OF THE INVENTION

Accordingly, an object of the invention is to provide a method and apparatus for synthesizing $N_2O_5$ and HMX by electrochemical means.

Another object of the invention is to provide a method and apparatus for synthesizing $N_2O_5$ and HMX using electrochemical means with improved current efficiency.

Yet another object of the invention is to provide a method and apparatus for synthesizing $N_2O_5$ and HMX without employing anhydrous $HNO_3$ at the anode.

Still a further object of the invention is to provide a method and apparatus for synthesizing $N_2O_5$ and HMX without employing anhydrous $HNO_3$ at the cathode.

Yet another object of the invention is to provide a method and apparatus for electrochemically synthesizing $N_2O_5$ and HMX, while minimizing side reactions in the electrochemical cell.

Additional objects, advantages, and novel features of the invention will be set forth in part in the description which follows, and in part will become apparent to those skilled in the art by examination of the following, or may be learned by practice of the invention. The objects and advantages of the invention may be realized and attained by means of the instrumentalities and combinations particularly pointed out in the appended claims.

To achieve the foregoing and other objects, and in accordance with the purpose of the present invention as embodied and broadly described herein, the apparatus for electrochemically synthesizing $N_2O_5$ includes means for housing the solution of $N_2O_4$ and $HNO_3$. Also included is a power source, and an anode disposed in an anode compartment of the housing means. The anode is operatively connected to the $N_2O_4/HNO_3$ solution and the power source. A cathode is disposed in a cathode compartment of the housing means, and operatively connected to the power source. A solution of $HNO_3$ is disposed within the cathode compartment. Means for maintaining a controlled potential between the $N_2O_4/HNO_3$ solution and the anode are included. In a further aspect of the present invention, the means for maintaining the controlled potential comprises a potentiostat operatively connected to the anode, cathode and the $N_2O_4/HNO_3$ solution.

In a further aspect of the present invention, and in accordance with its objects and purposes, the method of synthesizing $N_2O_5$ comprises providing an electrochemical cell including an anode disposed in an anode compartment and a cathode disposed in a cathode compartment. The anode and cathode are operatively connected to a power source. A solution of $N_2O_4$ and $HNO_3$ is disposed within the cell in the anode compartment, and a solution of $HNO_3$ in the cathode compartment. A controlled potential is applied and maintained between the $N_2O_4/HNO_3$ solution and the anode, ultimately resulting in the formation of $N_2O_5$.

In yet another aspect of the present invention, a method of synthesizing HMX comprises providing an electrochemical cell including a cathode disposed in a cathode compartment of the cell and an anode disposed in an anode compartment of the cell. The cathode and anode are operatively connected to a power source. A solution of $N_2O_4$ and $HNO_3$ is disposed in the anode compartment of the cell, and a solution of $HNO_3$ is disposed in the cathode compartment. A controlled potential is applied and maintained between the $N_2O_4/HNO_3$ solution and the anode. Application of the controlled potential results in the formation of $N_2O_5$ which is subsequently added to a solution of either 1,3,5,7-tetraacetyl-1,3,5,7-tetraazacyclooctane (hereinafter referred to as TAT) or DADN, and heated. This product is then added to water, resulting in the formation of HMX.

Application of the controlled potential within the electrochemical cell provides an efficient method of synthesizing $N_2O_5$, and ultimately HMX, which is of a lower cost than traditional chemical methods. By providing the controlled potential, a substantial improvement is realized in current efficiency. Whereas previous electrochemical methods have obtained only about 35% current efficiency, the method and apparatus of the present invention yields a current efficiency of up to about 67%. Side reactions at the anode and cathode which reduce the amount of $N_2O_5$ formed are minimized. Additionally, use of the controlled potential eliminates the need for anhydrous $HNO_3$ in the anode and cathode compartments of the cell.

BRIEF DESCRIPTION OF THE DRAWINGS

The accompanying drawings, which are incorporated and form a part of the Specification, illustrate various embodiments of the invention, and, together with the Description, serve to explain the principles of the invention.

DESCRIPTION OF THE INVENTION

When $N_2O_4$ is oxidized to $N_2O_5$ electrochemically, the overall cell reactions are represented as follows:

$$\text{Anode Reaction } N_2O_4 + 2HNO_3 \longrightarrow 2N_2O_5 + 2H^+ + 2e^- \quad (3)$$

$$\text{Cathode Reaction } 2HNO_3 + 2H^+ + 2e^- \longrightarrow N_2O_4 + 2H_2O \quad (4)$$

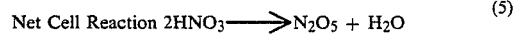
$$\text{Net Cell Reaction } 2HNO_3 \longrightarrow N_2O_5 + H_2O \quad (5)$$

Side reactions at the anode, such as the oxidation of the solvent $HNO_3$, are minimized by applying a controlled potential between the anode and the solution of $N_2O_4/HNO_3$ disposed in the anode compartment of the electrochemical cell. More particularly, the potential between the anode and the solution layer positioned adjacent to the anode is controlled and maintained at a predetermined value or range. DADN or TAT is then reacted with $N_2O_5$ to form HMX. Significantly, application of the controlled potential yields a current efficiency of up to about 67%.

Figure 1:
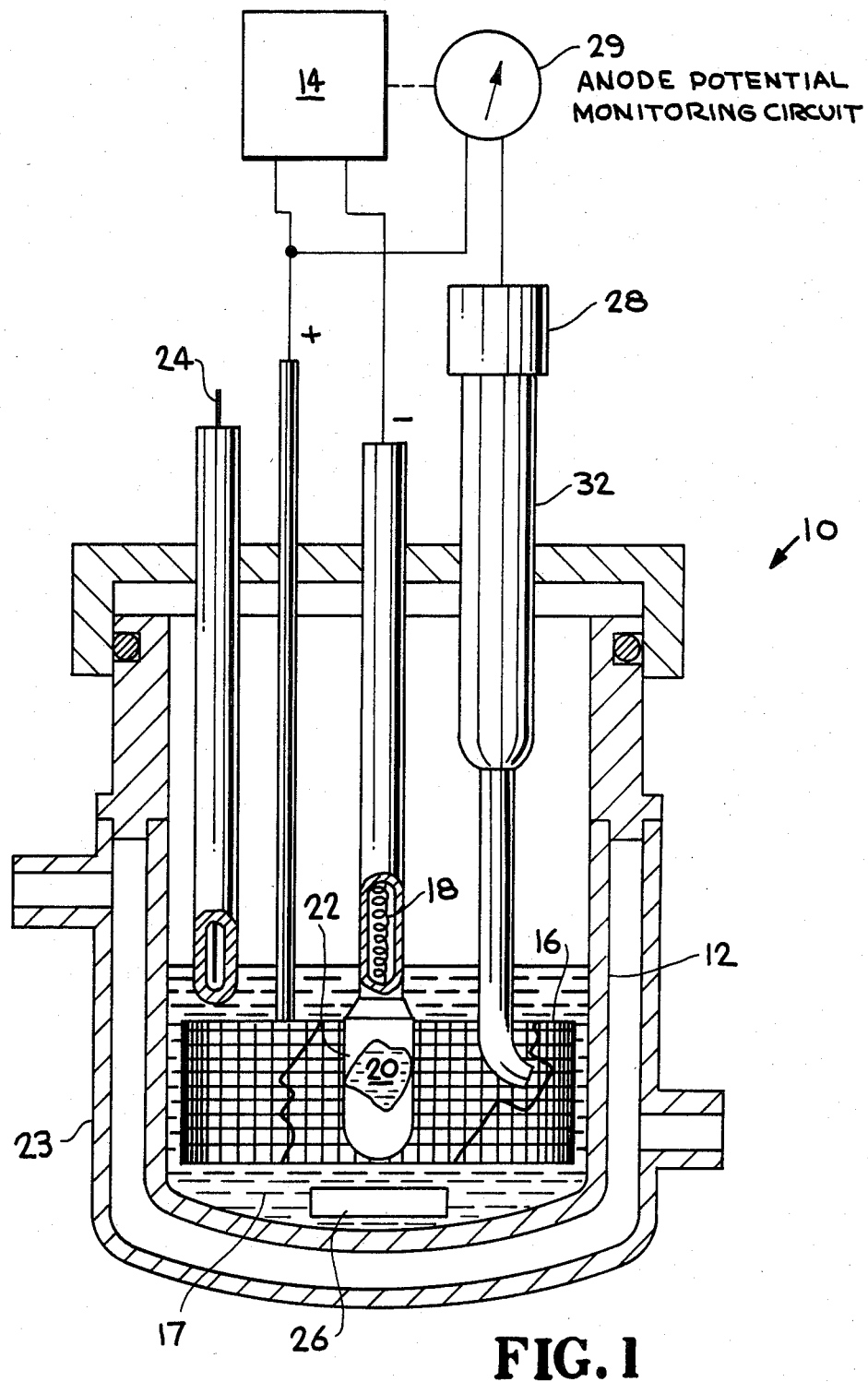
FIG. 1 illustrates schematically one embodiment of an electrochemical cell useful for the synthesis of $N_2O_5$ and HMX.

Referring now to FIG. 1, one embodiment of an electrochemical cell useful in the electrosynthesis of $N_2O_5$ is illustrated. Electrochemical cell 10 includes housing means 12 for containing a solution of $N_2O_4$ and $HNO_3$. A power source 14 is operatively connected to an anode 16 disposed within an anode compartment 17 of the electrochemical cell. The anode is partially disposed within and operatively connected to the $N_2O_4/HNO_3$ solution. A cathode 18 is disposed in a cathode compartment 20 of the housing means, and operatively connected to power source 14. Cathode 18 is separated from the $N_2O_4/HNO_3$ solution in anode compartment 17 by a semipermeable membrane 22 which allows for the passage of current between the anode and cathode, e.g., the passage of ions through the membrane between the two compartments. Membrane 22 is formed from an acid-resistant material.

Disposed within the cathode compartment is a solution of $HNO_3$. Previously, it was believed that nearly anhydrous $HNO_3$ was a requirement for the oxidation of $N_2O_4$. It has now been discovered that the $HNO_3$ solution within the anode housing need not be anhydrous. To this end, the $N_2O_4/HNO_3$ solution can have a water content of up to 12% by weight. Additionally, the water content of the $HNO_3$ disposed in cathode compartment 20 can also be up to 12% by weight.

Means 23 are included for maintaining electrochemical cell 10 at a desired temperature. Such means include, but are not limited to a cooling jacket 23 disposed in adjacent surrounding relationship to housing means 12, and adapted to receive a cooling medium such as water. A thermocouple 24 is included to monitor the temperature. Optionally disposed within housing means 12 is a magnetic stirring bar 26.

Means are included for maintaining a controlled potential between the $N_2O_4/HNO_3$ solution within cell 10 and anode 16. More particularly, the potential between anode 16 and the $N_2O_4/HNO_3$ solution layer positioned adjacent to the anode is controlled. In one embodiment of the invention, the means for maintaining the controlled potential include a reference electrode 28 operatively connected to an anode potential monitoring circuit 29. Suitable reference electrodes include a saturated calomel electrode (SCE), Ag/AgCl and $Hg/Hg_2SO_4$ electrodes. For purposes of description, all stated potentials disclosed herein shall be measured against the SCE. Reference electrode 28 is operatively connected to the $N_2O_4/HNO_3$ solution in cell 10 via a salt bridge 32 filled with a solution of $HNO_3$. Again, aqueous $HNO_3$ can be employed in the salt bridge.

In a second embodiment of the invention, the concentrations of the reactants, specifically $N_2O_4$, are monitored and controlled in order to control the potential between anode 16 and the $N_2O_4/HNO_3$ solution layer positioned adjacent to the anode.

Figure 2:
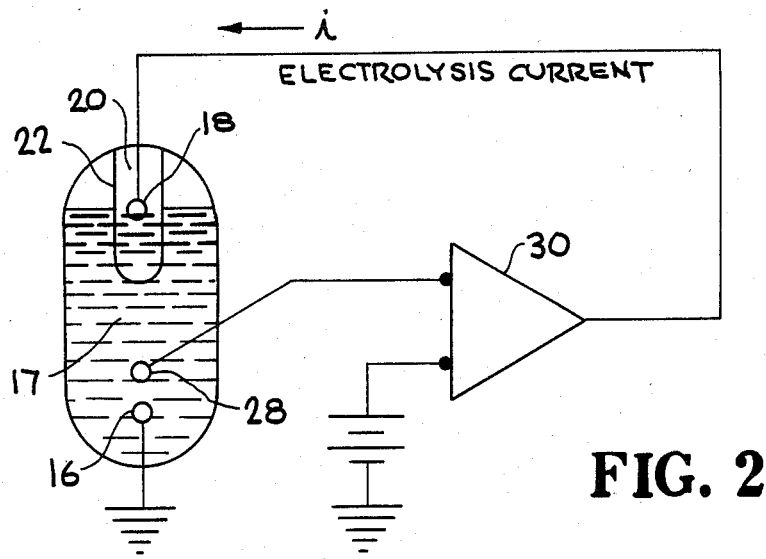
FIG. 2 illustrates schematically one embodiment of a controlled potential electrolysis system.

Referring to the schematic diagram of FIG. 2, a controlled potential electrolysis system is illustrated. A potentiostat 30 is operatively connected to anode 16 and cathode 18, as well as the solutions disposed in anode compartment 17 and cathode compartment 20. Potentiostat 30 essentially includes and combines the power source and anode potential monitoring circuit of FIG. 1. Membrane 22 again separates the solutions disposed in the anode and cathode compartments. The potential between anode 16 and reference electrode 28 is controlled. Electrolysis current flows between anode 16 and cathode 18, effecting the desired electrochemical reaction at anode 16. Reference electrode 28 is positioned nearly adjacent to anode 16, with the distance preferably minimized. The potential between the $N_2O_4/HNO_3$ solution within cell 10 and anode 16 is measured by reference electrode 28. The potential of reference electrode 28 is an accurately known value on a standard scale. Reference electrode 28 serves as a voltage sensor, measuring the potential of the $N_2O_4/HNO_3$ solution, more particularly, the voltage between anode 16 and the $N_2O_4/HNO_3$ solution layer positioned adjacent to the anode. The potential difference between this solution and anode 16, which determines the nature of the electrochemical reaction, is thus accurately known. A feedback control action of potentiostat 30 maintains the desired potential difference between anode 16 and the $N_2O_4/HNO_3$ solution layer adjacent to the anode as the electrolysis conditions fluctuate, by adjusting the voltage applied to cathode 18.

During $N_2O_4$ synthesis, controlling the potential prevents electrolysis of the $HNO_3$ solvent when all of the $N_2O_4$ has been consumed. The current efficiency, which is the percentage of the electrolysis current that performs the desired reaction, is thus maximized. A controlled potential, e.g., the potential between the anode and the $N_2O_4/HNO_3$ solution, is preferably about 1.35 to 2.00 V vs. SCE. More preferably, the controlled potential is about 1.50 to 1.90 V vs. SCE. Most preferably, the controlled potential is about 1.80 V vs. SCE, corresponding to a current density of about 100 $mA/cm^2$. Higher potentials would result in a faster rate of production of $N_2O_5$; however, the current efficiency would be reduced due to concurrent oxidation of the $HNO_3$.

Referring once again to FIG. 1, anode 16 and cathode 18 are each formed of a conductive material. Exemplary materials include Pt, $IrO_x$ on Ti, and $RuO_x$ on Ti, wherein x is 1 or 2. The working surface area of the cathode and anode can vary; however, the preferred ratio of area of anode to anode-compartment solution volume is about 1–3 $cm^2/ml$. Depending upon the amount of $N_2O_5$ required, the solution capability of electrochemical cell 10 can vary.

The method of synthesizing $N_2O_5$ includes providing an electrochemical cell such as cell 10 illustrated in FIG. 1, which includes an anode and cathode operatively connected to a power source. Thereafter, a solution of $N_2O_4$ in $HNO_3$ is disposed within the cell, and a controlled potential is applied and maintained between the solution and the anode. The result is the formation of $N_2O_5$. For this process, it has been discovered that a temperature of about 5°–25° C. is preferred. More preferably, the temperature is about 5°–10° C. The wt % of $N_2O_4$ to $HNO_3$ is preferably about 5–25, and more preferably about 10–15.

Before the electrolysis proceeds, $HNO_3$ and $N_2O_4$ are present in solution at anode 16. $N_2O_4$ dissociates as illustrated by the following equation:

$$N_2O_4 \rightleftharpoons 2NO_2 \rightleftharpoons NO^+ + NO_3^- \tag{6}$$

At the cathode, a solution of $HNO_3$ is present. During electrolysis, the following cathode reactions are possible:

$$2HNO_3 + 2H^+ + 2e^- \rightarrow N_2O_4 + H_2O \tag{7}$$

$$NO_3^- + 2H^+ + e^- \rightarrow NO_2H_2O \tag{8}$$

$$NO^+ + 2HNO_3 + e^- \rightarrow 3NO_2 + H_2O \tag{9}$$

$$2H^+ + 2e^- \rightarrow H_2 \tag{10}$$

The possible anode reactions are as follows:

$$NO_2 \rightarrow NO_2^+ + e^- \tag{11}$$

$$NO^+ + NO_3^- \rightarrow 2NO_2^+ + 2e^- \tag{12}$$

$$N_2O_4 + 2HNO_3 \rightarrow 2N_2O_5 + 2H^+ + 2e^- \tag{13}$$

The final solution at the anode comprises $HNO_3$ and $N_2O_5$, which dissociates as follows:

$$N_2O_5 \rightarrow NO_2^+ + NO_3^- \qquad (14)$$

In the final solution at the cathode, $H_2O/HNO_3$ and $N_2O_4$ are present. The $N_2O_4$ dissociates as shown in Equation (6).

In a further aspect of the present invention, the $N_2O_5$ formed from the electrolysis of $N_2O_4$ is utilized to synthesize HMX. In this method, an electrochemical cell which includes a cathode and an anode operatively connected to a power source is provided. Disposed within the cell is a solution of $N_2O_4$ and $HNO_3$. A controlled potential is applied and maintained between the $N_2O_4/HNO_3$ solution and the anode. $N_2O_5$ is formed by the application of the controlled potential. Thereafter, the $N_2O_5$ formed is added to a solution selected from DADN or TAT and heated. The product formed is added to water, resulting in the formation of HMX. Thereafter, the HMX is physically separated from the solution. In this method, the molar ratio of $N_2O_5$ to DADN or TAT is preferably about 3.6. Preferably, the temperature at which the DADN or TAT is reacted with the $N_2O_5$ is about 35°-45° C. More preferably, the temperature is about 40° C. The heating of DADN or TAT with $N_2O_5$ preferably continues for about 1 hour.

The following examples are meant to exemplify certain embodiments of the present invention, and are not regarded as limiting its scope which is defined in the appended claims.

$N_2O_5$ was synthesized under controlled potential conditions, as illustrated in Examples 1 through 11. The following experimental procedure was used for these Examples.

Electrolysis Equipment

Three sizes of electrolysis cells were used for the $N_2O_5$ preparations, each illustrated generally as in FIG. 1. The cathodes and anodes for most of the experiments were Engelhard grade E2 (99.95%) platinum gauze. Those not employing platinum electrodes used $IrO_x$ on titanium, where x is 1 or 2. The cell membrane was either Corning No. 7930 porous Vycor glass, or DuPont Nafion prefluorinated ion-exchange membrane. The three electrosynthesis cells were constructed with anode electrode planar areas, cell solution capabilities, and separator tube diameters as follows: 68 cm$^2$, 25 ml, 1 cm; 124 cm$^2$, 125 ml, 1.5 cm; and 180 cm$^2$, 225 ml, and 1.5 cm. The reference electrode used for all of the cells was an aqueous saturated calomel electrode whose potential was checked periodically against a laboratory-prepared standard. The salt bridge was terminated in a tip containing an asbestos fiber. This tip was drawn out to 1 mm diameter, and positioned approximately 1 mm from the anode. Both the salt bridge tube and cathode housing compartment were filled with anhydrous $HNO_3$. Potentiostats were used for the controlled potential electrosynthesis.

Reagents

Anhydrous nitric acid was prepared by distillation from a mixture of reagent grade 70% $HNO_3$ and concentrated $H_2SO_4$ (1:3 v/v) in a glass apparatus under reduced pressure and at room temperature. NMR analysis verified that the water content did not exceed 0.4%, the equilibrium concentration present in nominally anhydrous acid. The $N_2O_4$ was Air Products & Chemicals, Inc. CP grade.

Procedures

Solutions in the range of 5-20% $N_2O_4$ in $HNO_3$ were prepared by weight from the anhydrous $HNO_3$ in liquid $N_2O_4$ cooled in an ice bath.

During the electrosynthesis, the controlled potential was generally set to a value of approximately 100 mV less positive than the final value, and then raised gradually as the electrolysis proceeded, to maintain a more nearly constant rate of electrolysis and tighter temperature control. The controlled potential reported for these experiments in the nominal final control potential was uncorrected for uncompensated resistance. Power consumption was calculated from periodic measurements of the cell current and total voltage.

Chemical Analysis Methods

The initial solutions and solutions produced by electrolysis were examined by two different analytical techniques: high resolution Raman and NMR spectrometry.

Quantitative determinations of the concentrations of $N_2O_5$ produced by the electrolysis were performed using the method based on measurement of the proton chemical shift resulting from the presence of nitrate ions in the anhydrous $HNO_3$.

Figure 3:
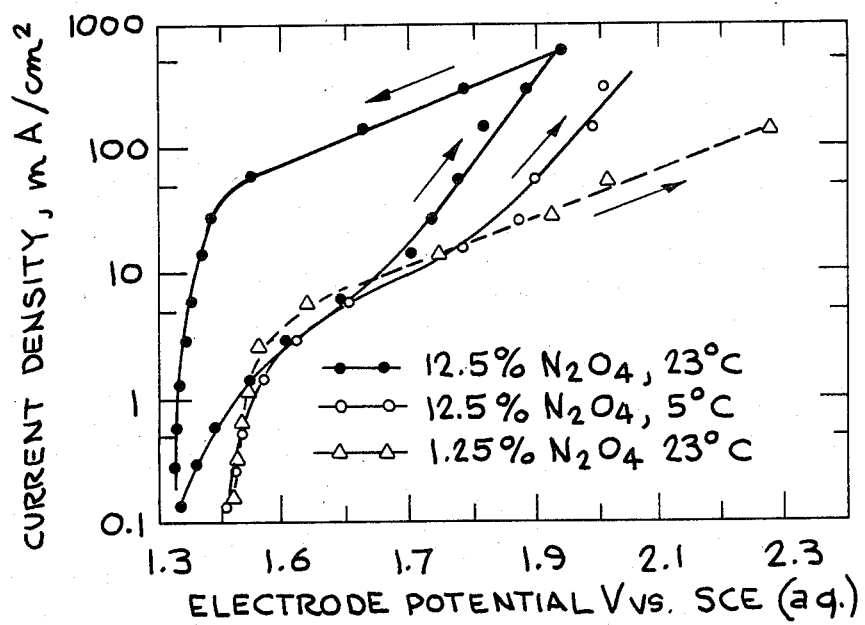
FIG. 3 is a graph plotting oxidation of $N_2O_4$ in the concentration range suitable for electrosynthesis, as shown, using Pt electrodes.

FIG. 3 illustrates a Tafel plot for the oxidation of $N_2O_4$ in the concentration range suitable for electrosynthesis using platinum electrodes. Current density was plotted against electrode potential. Three curves were obtained for: 12.5% $N_2O_4$ at 23° C.; 12.5% $N_2O_4$ at 5° C.; and 1.25% $N_2O_4$ at 23° C.

Figure 5:
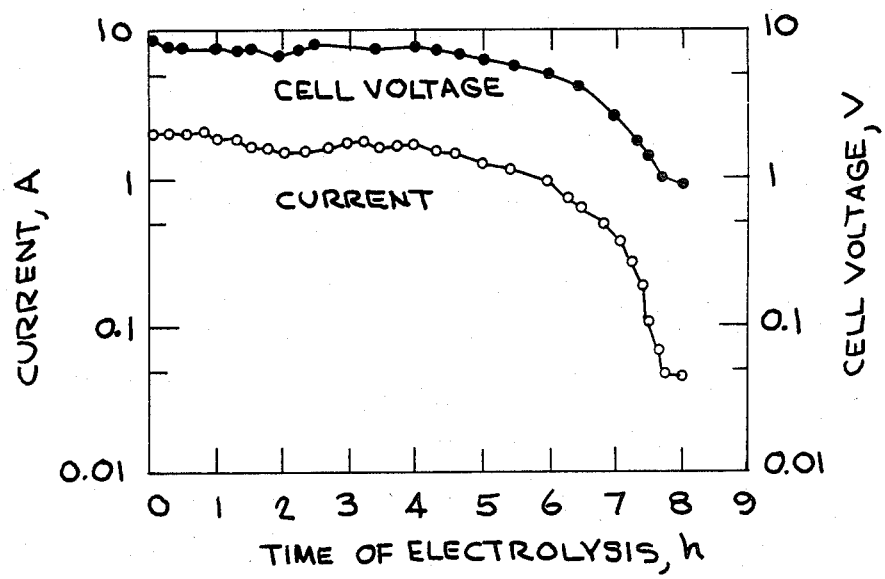
FIG. 5 is a graph plotting current vs. time of electrolysis for the oxidation of $N_2O_4$ to $N_2O_5$.

FIG. 5 is a current-time curve for the electrooxidation of $N_2O_4$ to $N_2O_5$ at high concentrations. At controlled potentials more negative than that of the decomposition of the $HNO_3$, (approximately 2.0 V vs. SCE), the current was nearly constant for about 80% of the time, then dropped to a relatively low value when all of the $N_2O_4$ has been consumed. Current was plotted against time of electrolysis expressed in hours.

The results of Examples 1-11 for the synthesis of $N_2O_5$ by controlled potential oxidation of $N_2O_4$ are summarized in Table I.

TABLE I

Representative results of the synthesis of $N_2O_5$ by controlled-potential oxidation of $N_2O_4$ in anhydrous $HNO_3$

| Initial $N_2O_4$ Cont. (wt. %) | Temp. (°C.) | Final Control Potential (V vs. SCE) | Peak Current (A) | Time of Electrolysis (h) | $N_2O_5$ in Anolyte (moles) | Final Conc. $N_2O_5$ (wt. %) | Mole ratio $N_2O_5$ $N_2O_4$ | MNO loss (%) | n (F per mole $N_2O_4$) | Product Current Efficiency (%)[b] | Specific Energy (kWh/mole $N_2O_5$) |
|---|---|---|---|---|---|---|---|---|---|---|---|
| 1.4[a] | 24 | 1.80 | 4.0 | 6 | 317 | 22.8 | 0.79 | 14.5 | 1.49 | 53 | 0.49 |
| 20.5 | 24 | 1.85 | 0.8 | 7.5 | 98.5 | 23.7 | 0.95 | 6.0 | 1.57 | 60 | 0.85 |
| 13.9 | 14 | 1.80 | 0.8 | 5 | 69.5 | 15.7 | 0.97 | 0.5 | 1.48 | 65 | 0.68 |
| 12.5[a] | 23 | 1.80 | 2.0 | 7 | 235 | 14.6 | 0.94 | 8.9 | 1.50 | 62 | 0.50 |
| 12.5[a] | 6 | 1.85 | 2.0 | 7.5 | 238 | 14.7 | 0.97 | 5.9 | 1.52 | 64 | 0.29 |

TABLE I-continued

Representative results of the synthesis of $N_2O_5$ by controlled-potential oxidation of $N_2O_4$ in anhydrous $HNO_3$

| Initial $N_2O_4$ Cont. (wt. %) | Temp. (°C.) | Final Control Potential (V vs. SCE) | Peak Current (A) | Time of Electrolysis (h) | $N_2O_5$ in Anolyte (moles) | Final Conc. $N_2O_5$ (wt. %) | Mole ratio $N_2O_5$ $N_2O_4$ | MNO loss (%) | n (F per mole $N_2O_4$) | Product Current Efficiency (%)[b] | Specific Energy (kWh/mole $N_2O_5$) |
|---|---|---|---|---|---|---|---|---|---|---|---|
| 10.8[a] | 25 | 1.90 | 1.9 | 7 | 175 | 11.1 | 0.80 | 8.6 | 1.46 | 55 | 0.42 |
| 10.5[a] | 25 | 1.95 | 3.5 | 3 | 179 | 12.0 | 0.87 | 12.6 | 1.40 | 62 | 0.67 |
| 9.8 | 22 | 1.78 | 0.7 | 4 | 43.3 | 11.75 | 1.03 | 1.4 | 1.54 | 67 | 0.55 |
| 5.1 | 24 | 1.79 | 0.6 | 2.5 | 26.9 | 6.05 | 1.01 | 0.0 | 1.57 | 65 | 0.86 |
| 1.57 | 25 | 1.80 | 0.28 | 2.5 | 7.9 | 1.85 | 1.01 | 0.0 | 1.73 | 59 | 0.48 |
| 1.59 | 25 | 1.56 | 0.10 | 7 | 7.8 | 1.82 | 0.98 | 0.0 | 1.73 | 57 | 0.77 |

[a]125-ml cell; other experiments with 25-ml cell.
[b]Based on equiv. wt. of $N_2O_5$ = mol. wt. $N_2O_5$.

EXAMPLE 12

Figure 4:
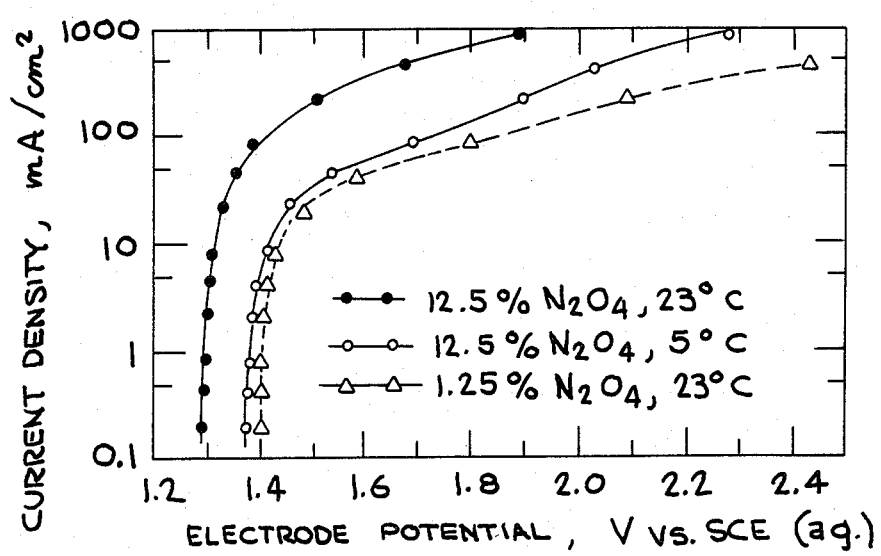
FIG. 4 is a graph plotting oxidation of $N_2O_4$ in the concentration range suitable for electrosynthesis, as shown, using $IrO_x$-coated titanium electrodes.

A solution of 13.9% $N_2O_5$ was prepared from 12.1% $N_2O_4$ using $IrO_x$-coated titanium electrodes, where x is 1 or 2, according to the procedure outlined in Examples 1–11 above. FIG. 4 illustrates a Tafel plot for the electrolysis. Current density was plotted against electrode potential. Three curves were obtained for: 12.5% $N_2O_4$ at 23° C.; 12.5% $N_2O_4$ at 5° C.; and 1.25% $N_2O_4$ at 23° C.

EXAMPLE 13

A solution of 13.4% $N_2O_5$ in aqueous $HNO_3$ was prepared from a solution of 33.3% $N_2O_4$, 11.5% $H_2O$ and 55.2% $HNO_3$, using the procedure outlined in Examples 1–11.

EXAMPLE 14

HMX was synthesized utilizing the $N_2O_5$ generated from Examples 1–11 above. 3.6 moles of $N_2O_5$ and 1 mole of DADN were heated to about 40° C. for approximately 1 hour. This product was then poured into water, and the resulting HMX which formed was filtered and removed from solution. An 87% yield was obtained.

EXAMPLE 15

HMX was synthesized utilizing the $N_2O_5$ generated from Examples 1–11 above. 3.6 moles of $N_2O_5$ and 1 mole TAT were heated to about 40° C. for approximately 1 hour. This product was then poured into water, and the resulting HMX which formed was filtered and removed from solution.

The foregoing description of preferred embodiments of the invention have been presented for purposes of illustration and description. It is not intended to be exhaustive or to limit the invention to the form disclosed, and obviously many modifications and variations are possible in light of the above teaching. The embodiments were chosen and described in order to best explain the principles of the invention in its practical application, to thereby enable others skilled in the art to best utilize the invention in various embodiments, and with various modifications as are suited to the particular use contemplated. It is intended that the scope of the invention be defined by the claims appended hereto.

We claim:

1. A method of synthesizing $N_2O_5$, comprising:
   (a) providing an electrochemical cell including an anode disposed in an anode compartment and a cathode disposed in a cathode compartment, said anode and cathode being operatively connected to a power source;
   (b) disposing a solution of $N_2O_4$ and $HNO_3$ in said anode compartment, and a solution of $HNO_3$ in said cathode compartment;
   (c) applying and maintaining a controlled potential between said $N_2O_4/HNO_3$ solution and said anode to minimize side reactions; and
   (d) thereafter forming $N_2O_5$ in said anode compartment.

2. The method of synthesizing $N_2O_5$ according to claim 1, wherein said potential is controlled and maintained by providing a potentiostat operatively connected to said $N_2O_4/HNO_3$ solution, said anode and said cathode.

3. The method of synthesizing $N_2O_5$ according to claim 2, further comprising maintaining said $N_2O_4/HNO_3$ solution at a temperature of about 5°–25° C.

4. The method of synthesizing $N_2O_5$ according to claim 2, further comprising maintaining said $N_2O_4/HNO_3$ solution at a temperature of about 5°–10° C.

5. The method of synthesizing $N_2O_5$ according to claim 4, wherein said controlled potential is about 1.35 to 2.00 V vs. SCE.

6. The method of synthesizing $N_2O_5$ according to claim 2, wherein said controlled potential is about 1.80 V vs. SCE.

7. The method of synthesizing $N_2O_5$ according to claim 4, wherein said $N_2O_4/HNO_3$ solution has a water content of no more than about 12%.

8. The method of synthesizing $N_2O_5$ according to claim 2, wherein the weight percent of $N_2O_4$ in said $N_2O_4/HNO_3$ solution is about 5–33.

9. The method of synthesizing $N_2O_5$ according to claim 2, wherein the weight percent of $N_2O_4$ to $N_2O_4/HNO_3$ solution is about 10–15.

* * * * *